US008945026B2

(12) United States Patent
Moser et al.

(10) Patent No.: US 8,945,026 B2
(45) Date of Patent: Feb. 3, 2015

(54) DEVICE AND METHOD FOR ASCERTAINING THE FORCE-DISPLACEMENT CHARACTERISTIC CURVE OF ONE OR MORE LIGAMENTS

(75) Inventors: Walter Moser, Kaufdorf (CH); Peter Ritschl, Vienna (AT); Holger Broers, Uplengen-Spols (DE)

(73) Assignee: Smith & Nephew Orthopaedics AG, Rotkreuz (CH)

( * ) Notice: Subject to any disclaimer, the term of this patent is extended or adjusted under 35 U.S.C. 154(b) by 2442 days.

(21) Appl. No.: 11/568,178

(22) PCT Filed: Apr. 20, 2005

(86) PCT No.: PCT/EP2005/004241
§ 371 (c)(1),
(2), (4) Date: Nov. 7, 2007

(87) PCT Pub. No.: WO2005/102178
PCT Pub. Date: Nov. 3, 2005

(65) Prior Publication Data
US 2008/0188934 A1      Aug. 7, 2008

(30) Foreign Application Priority Data

Apr. 22, 2004 (DE) .......................... 10 2004 019 655
May 25, 2004 (DE) .......................... 10 2004 025 612

(51) Int. Cl.
*A61B 5/103*      (2006.01)
*A61B 5/117*      (2006.01)
(Continued)

(52) U.S. Cl.
CPC ............. *A61B 17/025* (2013.01); *A61B 5/1076* (2013.01); *A61B 5/4533* (2013.01); *A61B 2017/0268* (2013.01); *A61B 2019/461* (2013.01); *A61B 2019/464* (2013.01); *A61B 2019/5437* (2013.01)

USPC .......................................... 600/587; 600/595

(58) Field of Classification Search
USPC ............. 600/587, 595; 606/53, 57; 623/13.13
See application file for complete search history.

(56) References Cited

U.S. PATENT DOCUMENTS 4,000,644  A  *  1/1977   Oppenheimer ................. 73/791
4,899,761  A       2/1990   Brown et al.
(Continued)

FOREIGN PATENT DOCUMENTS

DE         202 17 014 U1    1/2003
EP         1 226 788 A1     7/2002
WO         WO 00/78225 A1   12/2000

OTHER PUBLICATIONS

Search Report in corresponding German Application No. DE 10 2004 025 612.8, mailed Nov. 29, 2004.
(Continued)

*Primary Examiner* — Max Hindenburg
*Assistant Examiner* — Adam Eiseman
(74) *Attorney, Agent, or Firm* — Krieg DeVault LLP (57) ABSTRACT

An appliance (1) for tensioning ligaments, especially articular ligaments, of a human or animal body, having at least one handle (2), the or each handle (2) being in operative engagement with, in each case, a tensioning element (3) associated therewith, and with the or each handle (2) in each case a force indicator (4), which indicates a force exerted on a or each tensioning element (3) associated with the or each handle (2) on tensioning of one or more ligaments, and a displacement indicator (5), which indicates the excursion of the tensioning element (3) in question from a reference position, and with the or each force indicator (4) and/or with the or each displacement indicator (5) there is/are associated at least one marker (7A-7H), which is arranged to be detected without contact by a measurement value ascertainment system (20) associated with the appliance (1), and also a device (20), comprising the appliance (1), for ascertaining force-displacement characteristic curves of ligaments, and also a method of ascertaining them.

21 Claims, 4 Drawing Sheets

(51) Int. Cl.
*A61B 17/02* (2006.01)
*A61B 5/107* (2006.01)
*A61B 5/00* (2006.01)
*A61B 19/00* (2006.01)

(56) References Cited

U.S. PATENT DOCUMENTS

| | | | |
|---|---|---|---|
| 5,227,985 A * | 7/1993 | DeMenthon | 702/153 |
| 5,713,897 A * | 2/1998 | Goble et al. | 606/53 |
| 6,045,517 A * | 4/2000 | Williams | 600/587 |
| 2002/0156480 A1 | 10/2002 | Overes et al. | |
| 2003/0036764 A1 | 2/2003 | Hamada | |
| 2005/0038442 A1 | 2/2005 | Freeman | |

OTHER PUBLICATIONS

Translation of International Preliminary Report on Patentability, mailed Dec. 14, 2006.
Search Report for PCT Application No. PCT/EP2005/004241, mailed Aug. 29, 2005.

* cited by examiner

DEVICE AND METHOD FOR ASCERTAINING THE FORCE-DISPLACEMENT CHARACTERISTIC CURVE OF ONE OR MORE LIGAMENTS

CROSS-REFERENCE TO RELATED APPLICATIONS

This Application is a US National Phase of the International Application No. PCT/EP2005/004241 filed Apr. 20, 2005 designating the US and published in German on Nov. 3, 2005 as WO 2005/102178, which claims priority of German Patent Application No. 10 2004 019 655.9, filed Apr. 22, 2004, and to German Patent Application No. 10 2004 025 612.8, filed May 25, 2004.

The present invention relates to an appliance for tensioning ligaments and to a device for ascertaining a force-displacement relationship or a force-displacement characteristic curve of one or more ligaments, the afore-mentioned appliance being a substantial part thereof, and also to a method of ascertaining a force-displacement relationship or a force-displacement characteristic curve of one or more ligaments, in accordance with the preambles of claims 1, 10 and 15.

BACKGROUND OF THE INVENTION

1. Field of the Invention

Appliances for tensioning ligaments, especially articular ligaments, of a human or animal body are used for tensioning soft tissue structures in controlled manner in the case of an operation for the replacement of degenerated joints by artificial joints. Known examples thereof are the replacement of hip joints and knee joints and also the replacement of vertebrae by artificial joints.

2. Description of the Related Art

For the success of an operation for the replacement of a damaged joint by an artificial joint, it is important that the passive structures stabilising the artificial joint, that is to say the ligaments and the capsule which surrounds the joint, are correctly adjusted.

The relatively recent literature on the subject of joint replacement describes the importance, for operative success, of quantitative assessment of the capsule/ligament structures (cf., for example, "An In-Vivo Biomechanical Analysis of the Soft-Tissue Envelope of Osteoarthritic Knees" in "The Journal of Arthroplasty", Vol. 19, 2004). The findings collated in that document result in an operative technique which in general terms starts from the basis of the ligaments' being of constant stiffness.

However, in the investigations carried out therein, considerable variations of up to 30% were recorded in the stiffness of the capsule/ligament apparatus. The mechanical properties of the capsule/ligament apparatus accordingly vary greatly between individuals. In addition, these properties are dependent on the state of disease of the joint and on the end state of the capsule/ligament apparatus, especially—in the case of the knee—on the state of the posterior cruciate ligament. Accordingly, only approximate information can be provided for the distraction forces that are to be used. Differences arise as a result of, inter alia, the different leg weight to be moved, the age of the patient and the nature of the disease. Especially strong structures are to be expected in relatively young patients with post-traumatic arthrosis. In the case of senile arthroses and rheumatic diseases, the quality of the structures can be expected to drop.

If stability of the joint in flexion is not achieved during or after the operation, the result is that the kinematics of the artificial joint are not optimal. A known example thereof is in the case of replacement of the knee joint by an artificial joint, where an upper leg component slides forward on a lower leg component as the knee is increasingly flexed, which is exactly the opposite of the natural sequence of motion of the knee joint.

Optimum joint kinematics are to be expected in the case of ligament structures which are almost isometrically stressed. In terms of operative technique, this is achieved by establishing joint stability in two positions. In the case of replacement of a knee joint, the assessment is made in 90° flexion and in extension. Optimum stability of the joint can be found from a force-displacement characteristic curve in simple manner. At said "stability point", all the structures are only just lightly tensioned but not yet elastically extended. As already mentioned hereinbefore, that stability point is patient-specific. This consequently leads to its being necessary to record a force-displacement characteristic curve for the joint being operated on, so that the necessary information can be obtained for determination of the stability point. Because of the demands made of an operative instrument, it has not hitherto been possible to make a recording of such a kind.

According to the prior art, relatively simply constructed appliances are used for tensioning ligaments, some of which are also provided with a mechanical force indicator, for indicating the force with which a joint is distracted, and with an indicator of the distraction displacement, that is to say the distance through which two joint compartments are distracted. An appliance of such a kind for tensioning ligaments is shown, for example, in WO 00/78225 A1.

A further appliance for the distraction of ligaments stems from the Applicant. Said appliance consists of two distraction elements actuatable by means of two mutually independent handles by way of a helical compression spring. Excursion of the distraction elements is accomplished by means of a force produced by compression of the helical compression spring using the handle in question. In addition to the force exerted on the particular distraction element, the displacement that the element in question undergoes can also be read off on the appliance so that a corresponding force-displacement relationship can be established. Both the force and also the displacement that the distraction element undergoes are indicated on a scale mounted on the appliance and read by the operating surgeon.

Using the afore-mentioned appliances for tensioning ligaments, especially articular ligaments, it is not possible to record a precise force-displacement characteristic curve having a high point density. In addition to inaccuracies in reading, caused by the measurement values' being read off by the operating surgeon or assisting staff, it is not possible to produce the point density necessary for an exact characteristic curve because the duration of the operation would be disproportionately prolonged as a result.

SUMMARY OF THE INVENTION

The invention is accordingly based on the problem of providing an appliance for tensioning ligaments, with the aid of which appliance, in the context of a device also to be provided for ascertaining a force-displacement characteristic curve, a force-displacement characteristic curve can be ascertained with a precision that is as high as possible and accordingly a joint's stability point can be determined in optimum manner. A further problem of the invention is to provide a corresponding method of acquiring a force-displacement characteristic curve.

The problem is solved, in its first aspect, by an appliance for tensioning ligaments which has the features of claim 1 and, in respect of the device for ascertaining a force-displacement characteristic curve, by a device which has the features of patent claim 10. In respect of the method aspects, reference should be made to claim 15.

The appliance according to the invention for tensioning ligaments, especially articular ligaments, of a human or animal body comprises at least one handle, the one handle or, when a plurality of handles are present, each handle being in operative engagement with, in each case, a tensioning element associated with the handle in question. With the one handle or with each of the plurality of handles there is furthermore associated, in each case, a force indicator, which indicates a force exerted on a tensioning element associated with the handle when one or more ligaments are tensioned. With each tensioning element there is furthermore associated a displacement indicator, which indicates the excursion, from a reference position, of the tensioning element in question. A basic point of the invention is that with the one force indicator or with each of the plurality of force indicators and/or with the one displacement indicator or with each of the plurality of displacement indicators there is associated at least one marker which can be detected without contact by a measurement value ascertainment system associated with the appliance. Of course, with the two afore-mentioned indicators there can also be associated, in each case, a plurality of markers. By means of this arrangement, it is possible to record a force-displacement characteristic curve of one or more ligaments, especially articular ligaments, and accordingly to determine the stability point of a joint. Furthermore, the ascertainment of the measurement data without contact ensures that high sterility demands can be met during the operation.

In a preferred embodiment, the marker or markers comprise optical elements. Alternatively or additionally, the marker or markers can comprise magnetic and/or electromagnetic elements. Both optical elements and also magnetic and/or electromagnetic elements can be readily and precisely detected by associated devices, optical elements being the most readily detected although they require a free field of view to the apparatus; magnetic and/or electromagnetic elements are somewhat more complicated to detect but the field of view between the marker and the apparatus can be optically interrupted.

The or each tensioning element is preferably mechanically, electromotively, hydraulically, pneumatically or hydro-pneumatically actuatable. Operation of such a kind is in some instances, especially in the mechanical and electromotive case, relatively simple to accomplish in terms of construction; hydraulic, pneumatic or hydro-pneumatic operation offers the operator a high degree of convenience without any sources of electromagnetic interference (possibly interfering with sensitive electronic devices used in the operation) being present.

In a preferred embodiment, the actuation device for the tensioning element comprises a force-producing element, the measurement of the force acting on the tensioning element in question being accomplished by measurement of a displacement difference associated with the force-producing element in question. In addition, but also alternatively, the excursion from a reference position, which can be for example a zero position or the like, can also be measured. This embodiment ensures simple measurement with readily accessible measurement variables.

In an embodiment which is especially simple in terms of construction, the force-producing element is a helical compression spring. The advantage is economical manufacture and also a relatively high degree of robustness of the appliance according to the invention.

In order to ensure a high degree of freedom of movement for the operating surgeon in relation to the position of the joint being replaced, there is preferably mounted on the appliance for tensioning ligaments at least one marker for determining axis orientation of the appliance. The patient can accordingly be brought into a position that is expedient for the operating surgeon (matched to the situation in question) during the operation.

The afore-mentioned marker or markers for determining axis orientation comprise preferably magnetic and/or electromagnetic and/or optical elements, although the afore-mentioned markers are preferably subject to the same principle of operation as the other markers present in the appliance. This ensures simple measurement with minimum outlay in terms of apparatus.

Preferably, at least a sub-set of the markers present comprises retroreflective balls, which are part of an optical measurement system, for example of a surgical navigation system, and which (as a passive component) make it possible for the appliance to be easily handled and to have a low weight.

A further basic point of the invention is that a device for ascertaining a force-displacement relationship or a force-displacement characteristic curve of one or more animal or human ligaments, especially articular ligaments, comprises an appliance for tensioning ligaments in accordance with one or more embodiments of the appliance for tensioning ligaments that is described hereinbefore, and also means for detecting the markers and means for evaluating the ascertained data. A device of such a kind makes it possible to detect the markers without contact and accordingly to establish a force-displacement characteristic curve, the advantages in each particular case corresponding inter alia to those of the associated appliance.

In a preferred embodiment, the device further comprises a memory and a calculation unit, in which the ascertained and/or evaluated data and/or reference values are stored and evaluated. Alternatively or additionally, specific data relating to the spatial position of the ligament apparatus being surveyed can also be held in the memory. As a result, continuous measurement is made possible, with it being possible, especially when data relating to the spatial position of the ligament apparatus being surveyed are stored, for reference data to be made available.

Preferably, the determinations of position being carried out are made approximately simultaneously, that is to say as far as possible only with a delay caused by the processing unit or the unit on a level higher than the measuring unit. This delay generally arises, for example, as a result of the fact that commands cannot be carried out in a computer exactly in parallel but have to be carried out sequentially. There is, moreover, the possibility of delay times of the measuring apparatuses in question. The clock frequencies are, however, so high (especially in the case of computers) that these time delays between measurements are usually very small. The afore-mentioned measurements are the measurement of the force acting on a tensioning element or of the forces acting on the tensioning elements, measurement of the displacement difference associated with the tensioning element and/or of the excursion from a reference position or of displacement differences associated with the tensioning elements and/or excursions thereof from a reference position, and also, optionally, measurement of the axis orientation of the appliance for tensioning ligaments. The advantage of simultaneous measurement lies in the fact that the measurement accuracy of the force-displacement characteristic curve is increased because with each corresponding force value there is associated a displacement value which is measured simultaneously or almost simultaneously. The measurement of the axis orientation of the appliance for tensioning ligaments which is optionally carried out at the same time increases the flexibility for the operating surgeon because said appliance does not then have to be kept in one and the same axis orientation throughout the operation.

In a preferred embodiment, the appliance furthermore comprises means for ascertaining time-dependent changes in different measurement variables. Of particular interest are the time-dependent changes in forces exerted on associated tensioning elements and/or in displacement differences and/or excursions from a reference position, which displacement differences and/or excursions are associated with force-producing elements. As a result of measurement of the different variables in dependence on time, time-dependent changes in the ligament apparatus of the patient can be calculated and identified, by means of which viscoelastic properties of the biological tissue can be measured and assessed. Of course, the variables which can be considered over time and which also in some cases must be observed also include the axis orientation of the appliance for tensioning ligaments.

A preferred embodiment which is simple in terms of construction includes, when optical markers are used, a stereo camera for detecting the markers in question.

With respect to the method aspects, the problem of the present invention is solved, as already mentioned, by a method having the features of patent claim 15.

Accordingly, a basic point of the present invention is that a method of ascertaining a force-displacement relationship or a force-displacement characteristic curve of one or more animal or human ligaments, especially articular ligaments, comprises the following steps: determination of a force acting on a tensioning element or of forces acting on tensioning elements; determination of a displacement difference associated with the tensioning element or of displacement differences associated with the tensioning elements and/or of an excursion associated with the tensioning element or of excursions associated with tensioning elements from a reference position; and, optionally, determination of an axis position of an appliance for tensioning ligaments, at least one of the aforementioned determinations being carried out without contact. The advantages of the method according to the invention are brought about analogously to those of the appliance for tensioning ligaments and the device for ascertaining a force-displacement characteristic curve. As an example thereof, reference may be made at this point only to the advantageous sterility properties.

Preferably, the method steps comprising determination of a measurement value or another determination are carried out approximately simultaneously. As already mentioned hereinbefore, "approximately simultaneously" means being separated in time only by delay times or calculating times of the calculating unit, by signal propagation times or by any delay times of the measurement devices. The advantage is the high precision of the resulting curve.

At least one of the determinations preferably comprises an optical and/or magnetic and/or electromagnetic measurement method. At this point too, with respect to the advantages reference may be made to the advantages mentioned in the course of the description of the appliance.

Determination of the measurement values explained in greater detail hereinbefore is preferably carried out iteratively, in which case a force-displacement characteristic curve is accordingly ascertained as soon as the particular force acting on the corresponding tensioning element is varied. By means of a point density that can be determined by the operating surgeon, it is possible for the precision to be further increased, as a result of an increased density of points or an increased density of measurement values, in intervals that are of particular interest and, in intervals of lesser interest, for the duration of the operation to be reduced by recording a lower point density.

Preferably, the excursion of the tensioning element or elements from a reference position, for example a zero position, on applying a constant force to the tensioning element or on applying constant forces to the tensioning elements, or else the force or forces applied for a constant excursion from a reference position or zero position is ascertained in dependence on time. By that means, conclusions can be drawn regarding the viscoelastic properties of the biological tissue.

BRIEF DESCRIPTION OF THE DRAWINGS

Further advantages and useful properties of the invention are to be found in the dependent claims and also in the following description of preferred embodiments referring to the accompanying Figures, in which:

DETAILED DESCRIPTION OF THE PREFERRED EMBODIMENTS

Figure 1:
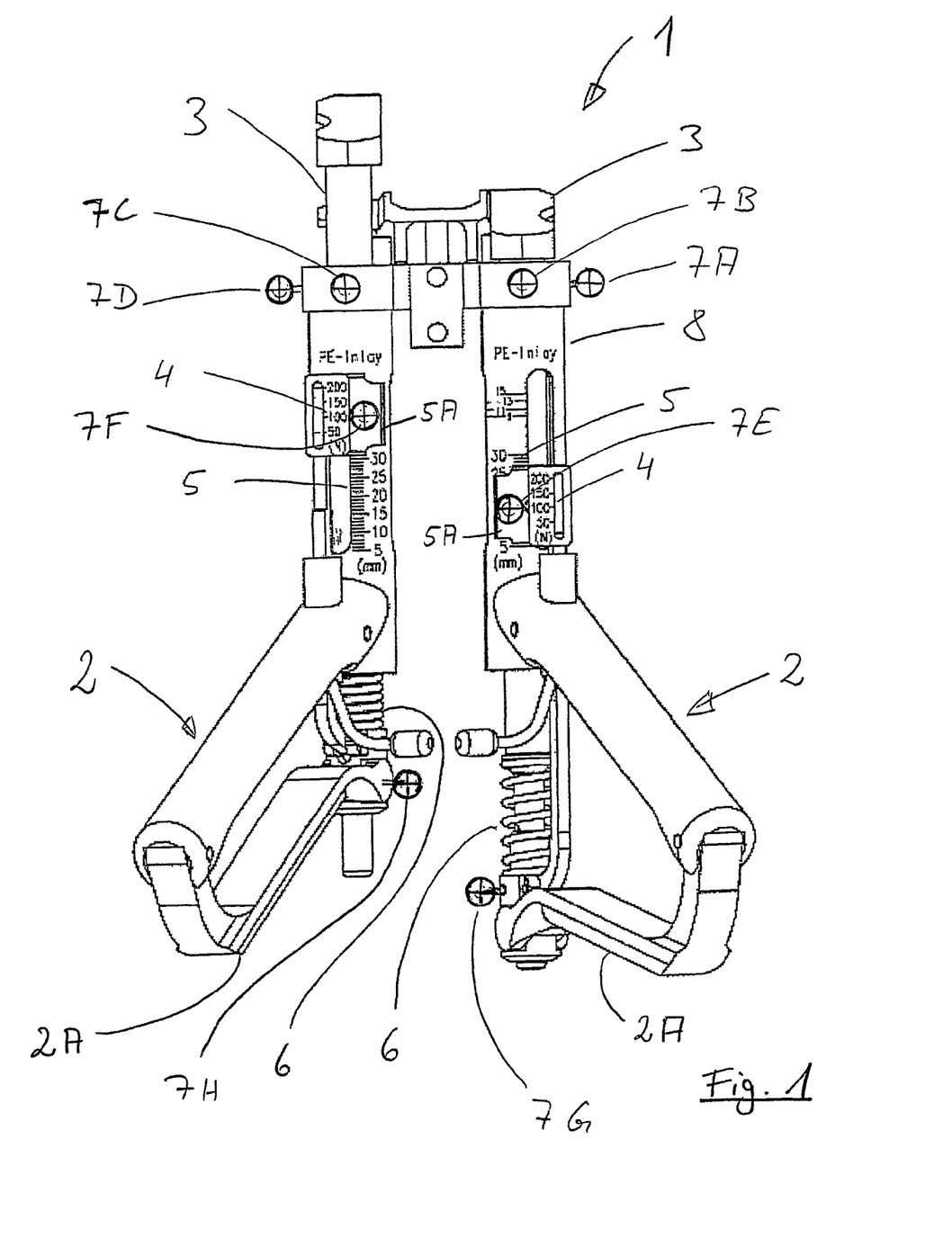
FIG. 1 shows a first embodiment of an appliance according to the invention for tensioning ligaments.

The appliance 1 shown in FIG. 1 for tensioning ligaments, in more precise terms for tensioning articular ligaments and for tensioning a capsule apparatus of a joint, has two handles 2. Each of those handles 2 is in operative engagement with, in each case, an associated tensioning element 3. With each of the two handles 2 there are furthermore associated, in each case, a force indicator 4 and a displacement indicator 5. Both the force indicators 4 and also the displacement indicators 5 have, in each case, an associated scale for reading off the values. The force indicators 4 show, in each case, the force exerted on the respectively associated tensioning element 3 by means of the associated handle 2, in more precise terms by means of a substantially vertically movable part 2A of the handle 2. The displacement indicators 5 represent the excursion of the respectively associated tensioning element 3 brought about by the force indicated on the respective force indicator 4.

As explained hereinbefore, the tensioning element 3 is, in the present exemplary embodiment, mechanically actuatable by means of the handles 2. It is to be noted that electromotive, hydraulic, pneumatic or hydro-pneumatic actuation would also be feasible. An actuation device for the respectively associated tensioning element 3 comprises a force-producing element, which in the present exemplary embodiment is in the form of a helical compression spring 6. When the helical compression spring is compressed by means of the handle 2, in more precise terms by means of the movable part 2A of the handle 2 (cf. especially the left-hand side of FIG. 1 in this respect), a force acts on the respectively associated tensioning element 3. By virtue of the force being applied, the tensioning element 3 undergoes excursion from a reference position in the form of a zero position or zero location.

Figure 3A:
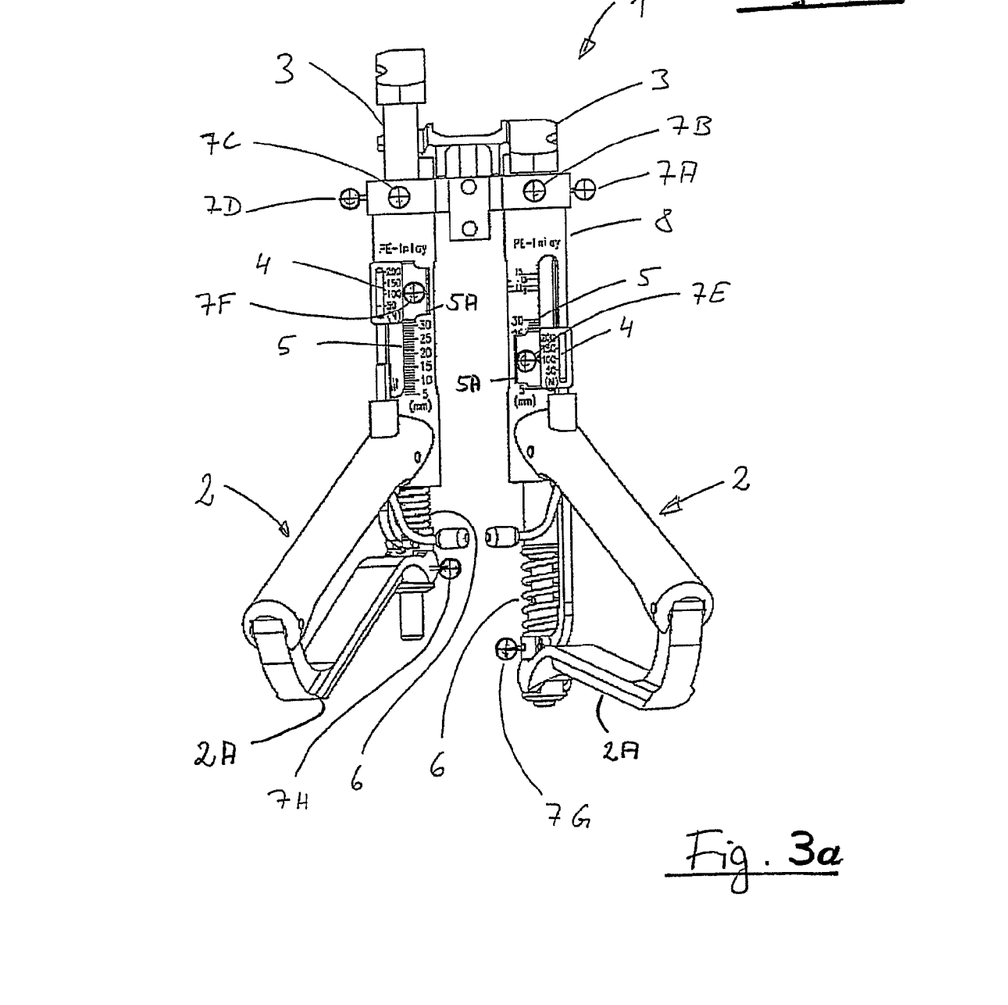
FIGS. 3a, b show an embodiment of a device for ascertaining a force-displacement relationship or a force-displacement characteristic curve, this device comprising an appliance for tensioning ligaments which is in accordance with FIG. 1.

On the appliance 1 there are furthermore mounted eight markers 7A-7H, which can be detected without contact by a measurement value ascertainment system (cf. also FIG. 3a in this respect) which is associated with the appliance and which will be explained in greater detail hereinafter. In the present exemplary embodiment, the markers 7A-7D are mounted on a housing of the appliance 1 and serve for determination of the axis orientation of the appliance 1. Two further markers 7E and 7F are in each case mounted on a slider 5A associated with the displacement indicator 5 and can be detected for the purpose of ascertaining the excursion of the respective tensioning element 3 from its reference position. Two further markers 7G and 7H are mounted on the lower, movable part of the handle 2 and serve to determine the spring tension by determining the length of the spring. By means of the known spring constant or spring characteristic of the helical compression spring 6 in question and the spring lengths established by means of the markers 7G and 7H, the force exerted on the respective tensioning element 3 can be established by simple means. The markers 7A-7H have, for (optical) detection by means of the associated device 20 (cf. FIG. 3b) passive optical elements in the form of retroreflective balls.

It should also be mentioned briefly that some or all of the markers 7A-7H can of course also comprise magnetic and/or electromagnetic elements, which allows detection of the positions that is just as precise. It should furthermore also be pointed out that it is of course not necessary for all the markers 7A-7H to function by the same principle of operation, that is to say optically, magnetically and/or electromagnetically, although preference is to be given to all the markers being subject to the same principle of operation. This ensures determination of positions with minimal outlay in terms of apparatus.

Figure 2:
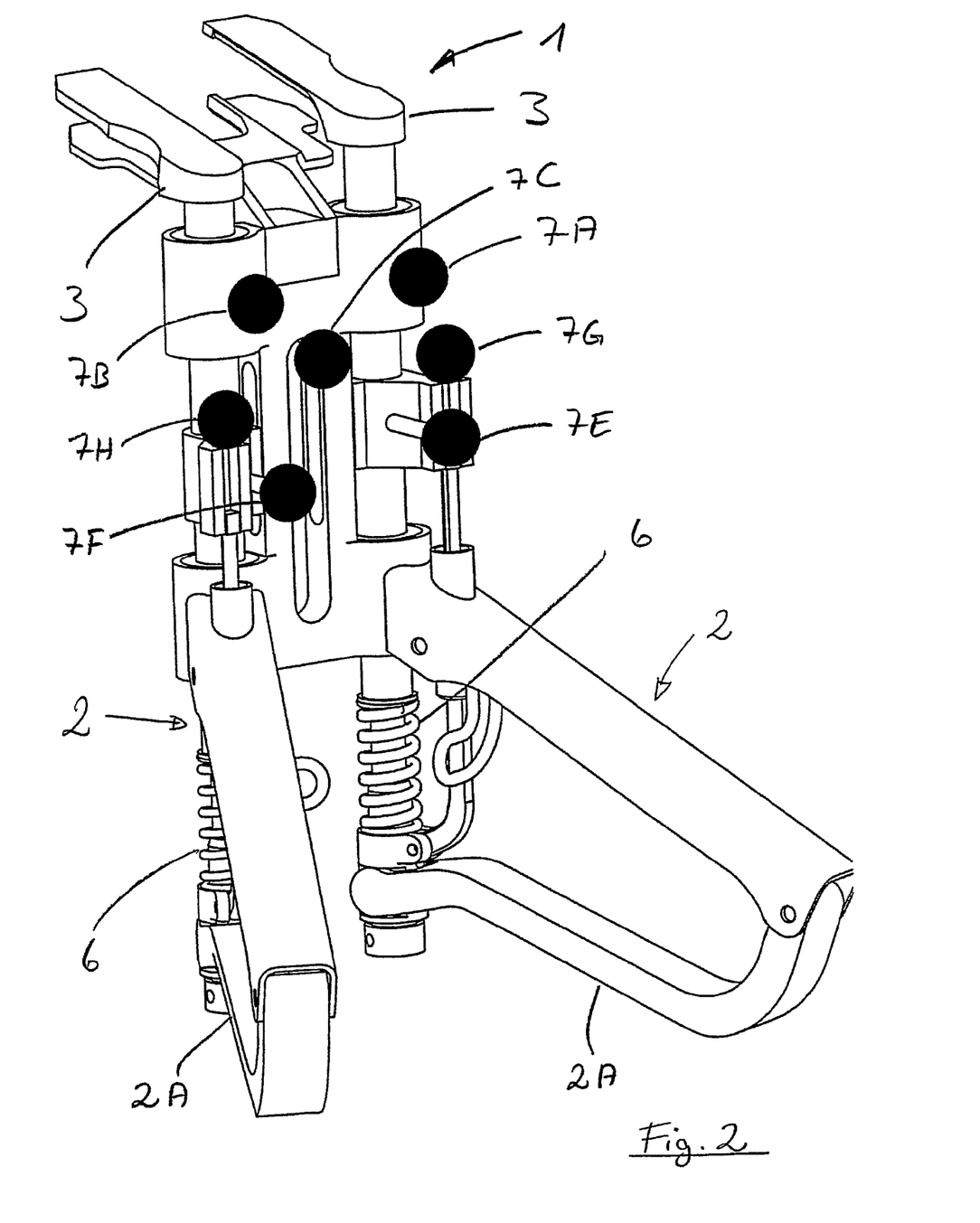
FIG. 2 shows a second embodiment of an appliance according to the invention for tensioning ligaments.

The appliance 1 shown in FIG. 2 for tensioning ligaments represents a further possible embodiment of an appliance 1 according to the invention for tensioning ligaments. Compared to the appliance 1 shown in FIG. 1, it is of somewhat simpler construction. The appliance 1 according to the second embodiment substantially comprises, again, two handles 2 having, in each case, an associated movable part 2A and, in each case, an associated helical compression spring 6, which exerts a force on an associated tensioning element 3. The principle of operation corresponds to that of the appliance 1 according to FIG. 1. For determination of the axis orientation, three markers 7A to 7C are mounted on a housing of the appliance 1. Two further markers 7E and 7F serve for ascertaining the excursion of the respective tensioning element 3 from its reference position. Finally, two further markers 7G and 7H are again mounted on the appliance 1, which analogously to the appliance shown in FIG. 1 serve to determine the spring tension by determining the length of the spring. As mentioned hereinbefore, the embodiment according to FIG. 2 is of slightly simpler construction compared to the embodiment according to FIG. 1. A scale associated with, in each case, the force indicator and with the displacement indicator is omitted, which ensures a structure that is simpler in terms of construction and a structure with a lower overall weight. An appliance 1 according to FIG. 2 is preferably usable in conjunction with a device 20 (explained in greater detail hereinbelow) for ascertaining a force-displacement characteristic curve, whereas the embodiment according to FIG. 1 also provides the possibility of the operating surgeon carrying out a visual reading in the event of failure of the device 20 or in the event of a device 20 not being available.

Figure 3B:
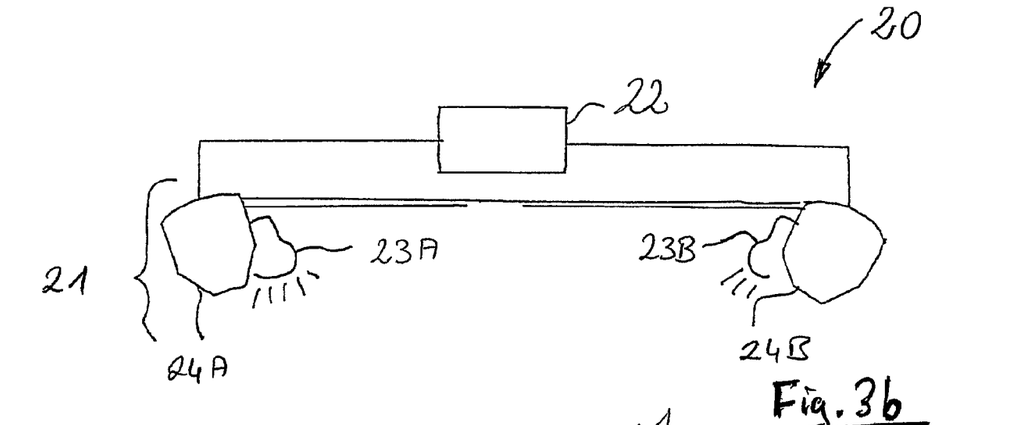

A complete device for ascertaining a force-displacement relationship or a force-displacement characteristic curve of one or more ligaments, especially articular ligaments, which can be, as already mentioned hereinbefore, animal or human in nature, is the device 20 shown in FIG. 3b. This includes, in the present embodiment, the appliance 1, already described hereinbefore, for tensioning ligaments and also means—in the form of a stereo camera arrangement 21—for detecting the markers and also means—in the form of an evaluation unit 22—for evaluating the data ascertained by the stereo camera arrangement 21. The basic components of the stereo camera arrangement 21 are two IR illumination sources 23A and 23B and also two IR cameras 24A and 24B. Of course, the use of another appliance 1 for tensioning ligaments is feasible, for example the use of an appliance 1 according to FIG. 2.

The evaluation unit 22 comprises a calculation unit, in which there is implemented a specific evaluation program, which allows overall evaluation of the light and/or IR signals coming from the markers 7A-7H in order to produce a positional data set in respect of both the axis orientation of the appliance 1 and the force exerted, in each case, on the tensioning elements 3 and also their excursion from the reference position.

The evaluation unit 22 furthermore comprises a memory for storage of the ascertained data and also of the evaluated data. Also stored are reference values and specific data, especially reference data relating to the spatial location of the ligament apparatus being surveyed.

Measurement of the three afore-mentioned variables, namely the forces acting, in each case, on the tensioning elements 3, the displacement distance undergone, in each case, by the tensioning elements 3 or the excursion of, in each case, the tensioning elements 3 from the reference position, and also measurement of the axis orientation of the appliance 1 for tensioning ligaments, is performed approximately simultaneously. In this context "simultaneously" means that only delay times of the measurement apparatuses in question, signal propagation times and also, in the case of sequential processing by the evaluating program, the time required by the processor of the evaluation unit 22 lie between the individual measurements. With the customary clock frequencies of processors and the short delay times of modern measurement apparatuses, the measurements can be regarded as simultaneous in a good approximation.

The device 20 is furthermore arranged for the purpose of measuring time-dependent changes in the forces exerted on the tensioning elements 3 in question and/or in the excursions of the force-producing elements from their reference positions in dependence on time. This means therefore that, for example, the excursion from the reference position of the tensioning element 3 whilst maintaining a constant force on the tensioning element 3 is recorded in dependence on time or the force acting on the tensioning element 3 in question whilst maintaining a constant excursion from a reference position is recorded in dependence on time. By this means, time-dependent changes in the ligament and capsule apparatus of a patient can be identified and accordingly viscoelastic properties of the biological tissue measured and assessed.

It should be noted that, in principle, three spatial scales can be read off using a single signalling means. In another embodiment of the here-presented appliance 1 for tensioning ligaments or of the device 10 for ascertaining a force-displacement relationship or a force-displacement characteristic curve, force and displacement measurements are determined using a single signalling means. For the purpose, the displacement measurement scale is oriented orthogonally to the force measurement scale. At the same time, the orientation of the anatomy can, if so required, be recorded (leg axis in x° flexion, that is to say angle of flexion, extension).

It should furthermore be noted that, in the case of the afore-mentioned embodiments, the accuracy of the force measurement is high because of a reduction ratio in the movable parts (as already described, the determination of force is carried out "indirectly" by way of determining a distance, namely the length of the spring). The reduction ratio works in such a manner that one millimeter of scale change in the afore-mentioned exemplary embodiments corresponds to a change in the length of the spring of 0.1 mm.

This reduces errors in the force measurement, especially errors caused by measurement tolerances. In the case of the force measurement, as already mentioned, the displacement is converted into a force using the characteristic curve of the spring tension, this practically constituting a case of indirect optical reading of a force.

Finally, the method on which the above-described appliance 1 and/or device 20 for ascertaining a force-displacement relationship or a force-displacement characteristic curve is based should be dealt with. By way of example, reference should be made to a diagram 30, which shows two force-displacement characteristic curves 31 and 32 in FIG. 4. The present example shows force-displacement characteristic curves 31, 32 of a human knee, the force-displacement characteristic curve 31 corresponding to the lateral side of the knee and the force-displacement characteristic curve 32 corresponding to the medial side of the knee. The "jagged" curves of the force-displacement characteristic curves 31 and 32 correspond to the measurement curves; the smooth, continuous lines correspond in each case to a polynomial fit. It is possible for the operating surgeon to derive the ideal pre-tensioning for the ligament-capsule apparatus from a force-displacement characteristic curve 31, 32 of such a kind.

Figure 4:
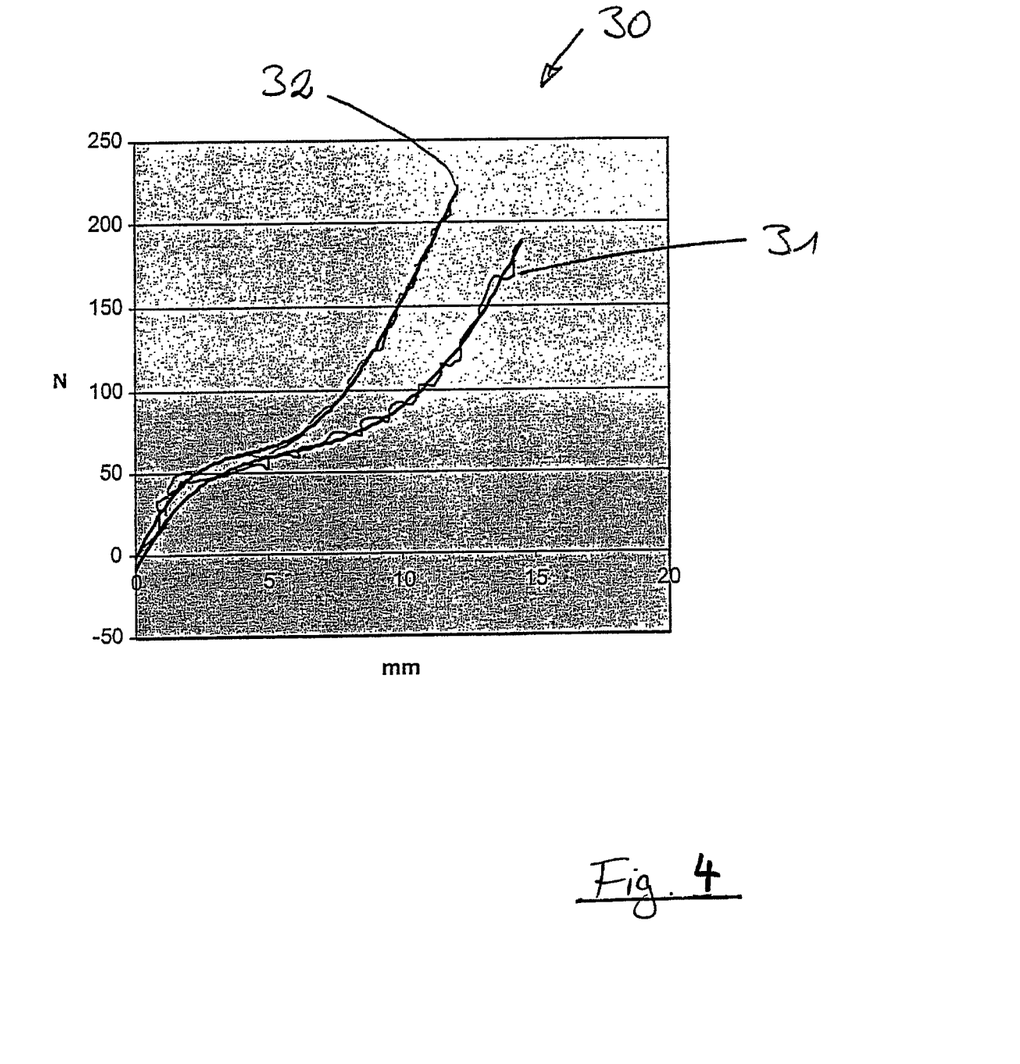
FIG. 4 shows an example of a force-displacement characteristic curve of a capsule and ligament apparatus.

The method of ascertaining a force-displacement relationship or a force-displacement characteristic curve 31, 32 comprises substantially the following steps: determination of the force acting in each case on a tensioning element 3, determination of the excursion, from a reference position, associated with the tensioning element 3 in question, and determination of an axis position of the appliance 1 for tensioning ligaments. Determination of the variables in question is carried out without contact. The determinations, described in greater detail hereinbefore, of the variables are also carried out approximately simultaneously, with "simultaneously" being understood in this context, as already mentioned hereinbefore, as meaning that the individual determinations are separated only by possible delay times of the measurement apparatuses, signal propagation times and by the time differences caused by the evaluation unit. The time differences caused by the evaluation unit 22 are substantially determined by the fact that the commands for measurement value determination and processing are in part processed sequentially in the evaluation unit 22. As a result of iteratively carrying out the steps mentioned in greater detail hereinbefore, the force-displacement characteristic curves 31 and 32 shown in FIG. 4 are obtained. Alternatively or additionally, depending on the requirements of the operating surgeon, it is possible to ascertain in dependence on time, by applying a constant force to the tensioning element 3, the excursion thereof from its reference position or, by keeping the excursion from the afore-mentioned reference position constant, the force acting on the tensioning element 3, which as already mentioned hereinbefore allows the measurement and assessment of viscoelastic properties of the biological tissue.

Although the invention is described with reference to exemplary embodiments having fixed combinations of features, it nevertheless also includes the possible further advantageous combinations of those features as set out especially, but not exhaustively, by the subordinate claims. All features disclosed in the application documents are claimed as being important to the invention insofar as they are novel on their own or in combination compared with the prior art.

LIST OF REFERENCE NUMERALS 1 appliance for tensioning ligaments
2 handle
2A movable part of handle 2
3 tensioning element
4 force indicator
5 displacement indicator
5A slider associated with displacement indicator 5
6 helical compression spring
7A-7H markers
8 housing
20 device for ascertaining a force-displacement characteristic curve
21 stereo camera arrangement
22 evaluation unit
23A, 23B IR illumination source
24A, 24B IR camera
30 diagram
31, 32 force-displacement characteristic curve

What is claimed is:

1. An appliance for tensioning articular or other ligaments of a human or animal body, said appliance comprising:
at least one handle;
a tensioning element associated with said at least one handle, the handle being in operative engagement with the tensioning element;
a force indicator associated with said at least one handle and configured to indicate a force exerted on the tensioning element upon tensioning of one or more ligaments;
at least one marker associated with the force indicator and configured to be detected without contact by a measurement value ascertainment system associated with the appliance, and wherein said at least one marker is configured to provide one or more non-electronic signals to the measurement value ascertainment system corresponding to the force indicated by the force indicator;
a displacement indicator associated with said at least one handle, said displacement indicator configured to indicate displacement of the tensioning element from a reference position; and
another marker associated with the displacement indicator, said another marker configured to be detected without contact by the measurement value ascertainment system, and wherein said another marker is configured to provide one or more non-electronic signals to the measurement value ascertainment system corresponding to the displacement indicated by the displacement indicator.

2. The appliance of claim 1, wherein the at least one marker comprises an optical element; and
wherein the at least one marker is in optical contact with the measurement value ascertainment system whereby the measurement value ascertainment system optically receives data from the at least one marker corresponding to the force indicated by the force indicator.

3. The appliance of claim 1, wherein the at least one marker comprises an element selected from the group consisting of magnetic elements, electromagnetic elements, and magnetic and electromagnetic elements; and wherein the at least one marker is in magnetic contact with the measurement value ascertainment system whereby the measurement value ascertainment system magnetically receives data from the at least one marker corresponding to at least one of the force indicated by the force indicator.

4. The appliance of claim 1, wherein the tensioning element is actuatable using a force selected from the group consisting of a mechanical actuation force, an electromotive actuation force, a hydraulic actuation force, a pneumatic actuation force, and a hydro-pneumatic actuation force.

5. The appliance of claim 1, wherein an actuator associated with the tensioning element comprises a force-producing element for applying a force to the tensioning element, said force associated with the force-producing element being determinable via a measurement selected from the group consisting of a displacement difference, excursion from a reference position, and a displacement difference and excursion from a reference position.

6. The appliance of claim 5, wherein the force-producing element is a helical compression spring.

7. The appliance of claim 1, wherein at least one of the markers comprises a retro-reflective ball.

8. The appliance of claim 1, wherein the measurement value ascertainment system includes:
a marker detector configured for detecting the at least one marker associated with the appliance; and
a data evaluator configured for evaluating data ascertained from said detection of the at least one marker.

9. A system for ascertaining a force-displacement relationship or a force-displacement characteristic curve of one or more animal or human articular or other ligaments, the system comprising:
an appliance configured for tensioning ligaments;
a marker detector configured for detecting at least one marker associated with the appliance; and
a data evaluator configured for evaluating data ascertained from said detection of the at least one marker; and
wherein the appliance comprises:
at least one handle;
a tensioning element associated with said at least one handle, the handle being in operative engagement with the associated tensioning element; and
a force indicator associated with said at least one handle and configured to indicate a force exerted on the tensioning element upon tensioning of one or more ligaments;
wherein the at least one marker is associated with the force indicator and is configured to be detected without contact with the marker detector and data evaluator, and wherein said at least one marker is configured to provide one or more non-electronic signals to the marker detector corresponding to the force indicated by the force indicator;
a displacement indicator associated with said at least one handle, said displacement indicator configured to indicate displacement of the tensioning element from a reference position; and
another marker associated with the displacement indicator, said another marker configured to be detected without contact by the marker detector and data evaluator, and wherein said another marker is configured to provide one or more non-electronic signals to the marker detector and data evaluator corresponding to the displacement indicated by the displacement indicator.

10. The system of claim 9, further comprising a memory for storing data selected from the group consisting of ascertained data, evaluated data, reference data, specific data relating to the spatial location of the ligament apparatus being surveyed, and any combination thereof.

11. The system of claim 9, wherein said appliance and marker detector are configured to provide a force measurement of a force acting on the tensioning element of the appliance, a distance measurement selected from the group consisting of a displacement difference associated with the tensioning element and an excursion from a reference position associated with the tensioning element, and an orientation measurement of the axis of orientation of the appliance approximately simultaneously.

12. The system of claim 11, further comprising a unit configured to ascertain time-dependent changes in at least one of forces exerted on the tensioning element, displacement differences associated with the tensioning element, and excursions from a reference position, said displacement differences and excursions being associated with a force producing element associated with the tensioning element.

13. The system of claim 9, wherein the at least one marker comprises an optical marker and the marker detector comprises a stereo camera.

14. The appliance of claim 1, wherein the at least one marker is not in electrical contact with the measurement value ascertainment system.

15. The system of claim 9, wherein the at least one marker is not in electrical contact with the marker detector.

16. The appliance of claim 1, further comprising a first of said at least one handle and a second of said at least one handle; and
wherein each of said first and second handles is associated with corresponding ones of said tensioning element, said force indicator, and said at least one marker.

17. The appliance of claim 16, wherein said at least one marker associated with said first handle provides a first non-electronic signal to the measurement value ascertainment system corresponding to the force indicated by the force indicator associated with said first handle; and
wherein said at least one marker associated with said second handle provides a second non-electronic signal to the measurement value ascertainment system corresponding to the force indicated by the force indicator associated with said second handle.

18. The appliance of claim 16, wherein the force indicated by the force indicator associated with the first handle corresponds to tensioning of a first ligament; and
wherein the force indicated by the force indicator associated with the second handle corresponds to tensioning of a second ligament.

19. The system of claim 9, further comprising a first of said at least one handle and a second of said at least one handle; and
wherein each of said first and second handles is associated with corresponding ones of said tensioning element, said force indicator, and said at least one marker.

20. The system of claim 19, wherein said at least one marker associated with said first handle provides a first non-electronic signal to the measurement value ascertainment system corresponding to the force indicated by the force indicator associated with said first handle; and
wherein said at least one marker associated with said second handle provides a second non-electronic signal to the measurement value ascertainment system corresponding to the force indicated by the force indicator associated with said second handle.

21. The system of claim 19, wherein the force indicated by the force indicator associated with the first handle corresponds to tensioning of a first ligament; and wherein the force indicated by the force indicator associated with the second handle corresponds to tensioning of a second ligament.

\* \* \* \* \*